(12) United States Patent
Chen et al.

(10) Patent No.: US 11,324,689 B2
(45) Date of Patent: *May 10, 2022

(54) COSMETIC COMPOSITIONS CONTAINING AN ALKOXYSILANE AND A SILSESQUIOXANE RESIN

(71) Applicant: L'OREAL, Paris (FR)

(72) Inventors: Michell Chen, Edison, NJ (US); Bayle Augustin, Union, NJ (US); Xiang Zhu, Manalapan, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/800,090

(22) Filed: Feb. 25, 2020

(65) Prior Publication Data

US 2020/0246247 A1 Aug. 6, 2020

Related U.S. Application Data

(63) Continuation of application No. 13/719,958, filed on Dec. 19, 2012, now Pat. No. 10,596,100.

(51) Int. Cl.
| | |
|---|---|
| *A61Q 5/06* | (2006.01) |
| *A61K 8/891* | (2006.01) |
| *A61K 8/23* | (2006.01) |
| *A61K 8/365* | (2006.01) |
| *A61K 8/58* | (2006.01) |

(52) U.S. Cl.
CPC ............. *A61K 8/891* (2013.01); *A61K 8/23* (2013.01); *A61K 8/365* (2013.01); *A61K 8/585* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 4,507,278 A | 3/1985 | DeMarco et al. |
| 4,698,065 A | 10/1987 | Hoeffkes et al. |
| 4,844,711 A | 7/1989 | Hoppe et al. |
| 5,108,738 A | 4/1992 | Halloran et al. |
| 5,152,984 A | 10/1992 | Varaprath et al. |
| 5,160,730 A | 11/1992 | Dubief et al. |
| 5,180,584 A | 1/1993 | Sebag et al. |
| 5,275,755 A | 1/1994 | Sebag et al. |
| 5,344,076 A | 9/1994 | Mercurio |
| 5,637,306 A | 6/1997 | Cauwet et al. |
| 5,733,537 A | 5/1998 | Halloran et al. |
| 5,879,414 A | 3/1999 | Milazzo |
| 6,162,424 A | 12/2000 | Decoster et al. |
| 6,306,182 B1 | 10/2001 | Chan et al. |
| 6,368,584 B1 | 4/2002 | Garnier et al. |
| 6,551,361 B1 | 4/2003 | Cornwell et al. |
| 6,953,572 B1 | 10/2005 | Samain et al. |
| 6,953,584 B1 | 10/2005 | Samain et al. |
| 7,037,347 B2 | 5/2006 | Kuzuhara et al. |
| 7,122,062 B2 | 10/2006 | Yamashita et al. |
| 7,176,170 B2 | 2/2007 | Dubief et al. |
| 7,223,384 B1 | 5/2007 | Decoster et al. |
| 7,244,420 B1 | 7/2007 | Samain et al. |
| 7,740,664 B2 | 6/2010 | Benabdillah et al. |
| 7,811,552 B2 | 10/2010 | Maubru et al. |
| 7,909,892 B2 | 3/2011 | Lautenbach et al. |
| 8,343,238 B1 | 1/2013 | Lopez et al. |
| 2004/0045099 A1 | 3/2004 | Kuzuhara et al. |
| 2004/0185020 A1 | 9/2004 | Gawtrey et al. |
| 2005/0071932 A1 | 4/2005 | Lautenbach et al. |
| 2007/0093619 A1 | 4/2007 | Bui et al. |
| 2007/0297996 A1 | 12/2007 | Tanner |
| 2008/0226576 A1 | 9/2008 | Benabdillah et al. |
| 2009/0291058 A1 | 11/2009 | Woodland et al. |
| 2009/0293899 A1 | 12/2009 | Woodland et al. |
| 2010/0083446 A1 | 4/2010 | Bonnamy et al. |
| 2010/0254932 A1 | 10/2010 | Benabdillah et al. |
| 2011/0110991 A1 | 5/2011 | Garrison et al. |
| 2011/0158927 A1 | 6/2011 | Viravau et al. |

FOREIGN PATENT DOCUMENTS

| | | |
|---|---|---|
| CN | 101069673 A | 11/2007 |
| EP | 0560682 A1 | 9/1993 |
| EP | 1862198 A2 | 12/2007 |
| FR | 2789896 A1 | 8/2000 |
| JP | 60004116 A | 1/1985 |
| JP | 7330556 A | 12/1995 |
| JP | 9175960 A | 7/1997 |
| JP | 9278636 A | 10/1997 |
| JP | 2001220322 A | 8/2001 |
| JP | 2002326916 A | 11/2002 |
| JP | 2003128527 A | 5/2003 |
| JP | 2004217672 A | 8/2004 |
| JP | 2006169163 A | 6/2006 |
| JP | 2006169164 A | 6/2006 |
| JP | 2008273869 A | 11/2008 |
| JP | 2012528139 | 11/2012 |
| WO | 9960993 | 12/1999 |
| WO | 2008020730 A1 | 2/2008 |
| WO | 2010089228 A1 | 8/2010 |
| WO | 11074144 A1 | 6/2011 |
| WO | 2012079873 A2 | 6/2012 |

OTHER PUBLICATIONS

U.S. Appl. No. 13/719,958, filed Dec. 19, 2012, Michell Chen et al.
U.S. Appl. No. 61/296,561, filed Jan. 20, 2010, Guillaume Cassin et al.
U.S. Appl. No. 61/296,563, filed Jan. 20, 2010, Guillaume Cassin et al.
U.S. Appl. No. 60/907,309, filed Mar. 28, 2007, Isabelle Rollat-Corvol et al.

(Continued)

Primary Examiner — Nissa M Westerberg
(74) Attorney, Agent, or Firm — Polsinelli PC (57) ABSTRACT

The present invention relates to composition for styling hair comprising: (a) a first phase comprising: at least one alkoxysilane having at least one solubilizing functional group and at least one amino substituent; at least one water-soluble metal salt; at least one acidifying agent; and at least one cosmetically acceptable carrier comprising water; and (b) a second phase comprising: at least one silsesquioxane resin and at least one volatile solvent. The present invention also relates to methods of styling hair.

19 Claims, 5 Drawing Sheets (56) References Cited

OTHER PUBLICATIONS

U.S. Appl. No. 61/064,400, filed Mar. 4, 2008, Katarina Benabdillah et al.
U.S. Appl. No. 61/259,757, filed Nov. 10, 2009, Gregory Plos et al.
U.S. Appl. No. 60/603,300, filed Feb. 26, 2007, Isabelle Rollat-Corvol et al.
U.S. Appl. No. 09/926,037, filed Feb. 3, 2000, Henri Samain et al.
European Patent Office, P.B. 5818 Patentlaan 2, NL-2280 HV Rijswijk, International Search Report issued in PCT Application No. PCT/EP2013/076848, dated May 6, 2014.
Kim, Jeong Tai, et al. "3-Aminopropyiltriethoxysilane effect on thermal and mechanical properties of multi-walled carbon nanotubes reinforced epoxy composites." Journal of composite materials 43.22, 2009, pp. 2533-2541.
Singha, A.S., et al. "Effect of aminopropyltriethoxysilane (APS) treatment on properties of mercerized lignocellulosic grewia optiva fiber." Journal of Polymers and the Environment 21.1, 2013, pp. 141-150; Available online Apr. 17, 2012.
Organosilicon page from Chemical Book (https://www.chemicalbook.com/ProductCatalog_EN/1326.htm) accessed Sep. 11, 2017.

1% APTES Solution

FIG. 1

1% APTES + Lactic Acid Solution

FIG. 2

5% APTES + Lactic Acid Solution

FIG. 3

Hair Treated with Water

FIG. 4

Hair Treated Inventive Composition

FIG. 5

COSMETIC COMPOSITIONS CONTAINING AN ALKOXYSILANE AND A SILSESQUIOXANE RESIN

CROSS-REFERENCE TO RELATED APPLICATIONS

This application claims priority to and is a continuation of U.S. patent application Ser. No. 13/719,958, filed on Dec. 19, 2012, entitled "COSMETIC COMPOSITIONS CONTAINING AN ALKOXYSILANE AND A SILSESQUIOXANE RESIN," the entirety of which is herein incorporated by reference.

TECHNICAL FIELD

The present invention relates to a composition and method of styling hair wherein the composition contains an alkoxysilane having at least one solubilizing functional group and an amino substituent, a water-soluble metal salt, an acidifying agent, and a silsesquioxane resin.

BACKGROUND OF THE DISCLOSURE

Consumers of cosmetic products actively seek out multifunctional, new products which are pleasing to the senses, both on application and in use, and which do not sacrifice the functional performance. One important functional element of such compositions is their ability to style the hair without weighing it down. Many consumers seek hair products which have excellent style memory, cosmeticity, and shine without heavily coating the hair strands, and thereby weighing the hair down and often times exhibiting a brittle or crunchy film. The resulting feel and texture of the hair after the application are important elements of such commodities. While different technologies and products exist in the market for hair styling products, there is still a need for improvement in these areas.

Traditional hair cosmetic treatment compositions on the market appear in various forms. They can range anywhere from solutions, foams, gels, creams, waxes, serums, to aerosols and can impart a variety of levels of conditioning depending on the state of the hair. However, these conventional cosmetic compositions have limitations and thus are less appealing to the consumer. Such limitations may include sticky or greasy products, irritation on the scalp, a heavy or oily coating on the hair, leading to decreased style memory or hair that lacks volume and a clean feel. Therefore, there is still a need to improve currently marketed commodities in order to provide the consumer with innovative formulations that present both sensory and functionality perspectives on hair treatment products.

Thus, the object of this invention is related to a composition and method of styling hair utilizing hair compositions which will impart shine benefits, volume, and good style memory to the hair, but will not result in any product build up or leave the hair feeling heavily coated, crunchy, or brittle.

BRIEF SUMMARY OF THE DISCLOSURE

It has surprisingly been found that compositions and methods of styling hair using a two phase system comprising at least one alkoxysilane having at least one solubilizing functional group and an amino substituent, at least one water-soluble metal salt, at least one acidifying agent, and at least one silsesquioxane resin impart styling benefits to the hair. The hair treatment composition is also emulsifier free.

Thus, the present invention is directed to a cosmetic composition for treating hair containing:
 (a) a first phase comprising:
  i. at least one alkoxysilane having at least one solubilizing functional group and at least one amino substituent;
  ii. at least one water-soluble metal salt;
  iii. at least one acidifying agent; and
  iv. a cosmetically acceptable carrier comprising water;
 (b) a second phase comprising:
  i. at least one silsesquioxane resin; and
  ii. at least one volatile solvent.

The present invention is also directed to a method of styling hair involving contacting the hair with the above-described composition.

DETAILED DESCRIPTION OF THE DISCLOSURE

Figure 1:
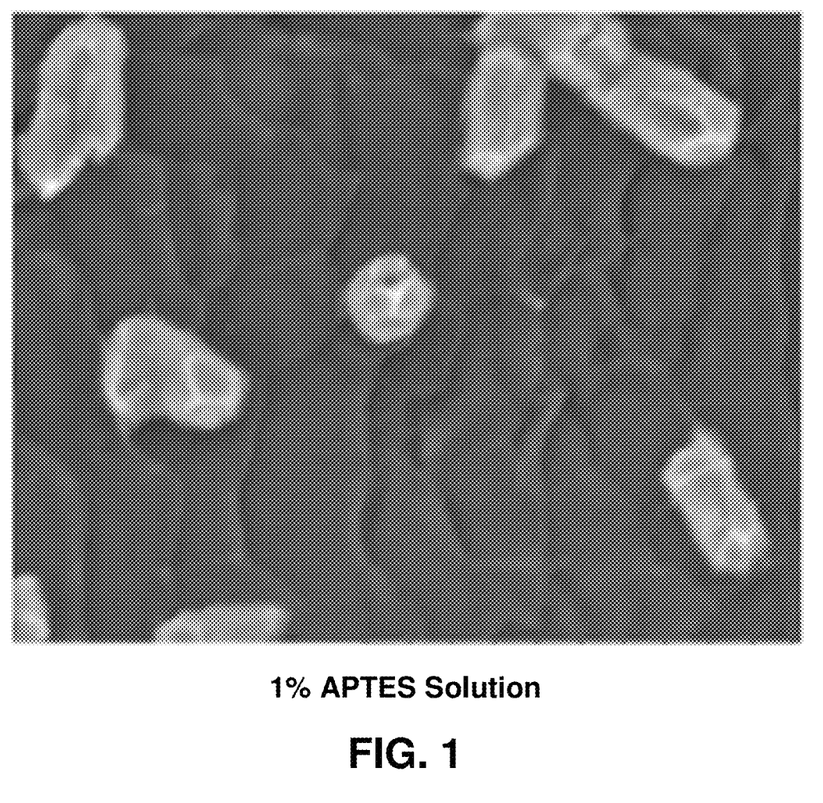
FIG. 1 is a scanning electron microscopy (SEM) image which shows the surface of hair treated by 1% by weight in water of an alkoxysilane having at least one solubilizing functional group and at least one amino substituent (3-aminopropyltriethoxysilane, "APTES"). The image shows many solid depositions of APTES on the dry hair surface.
Figure 2:
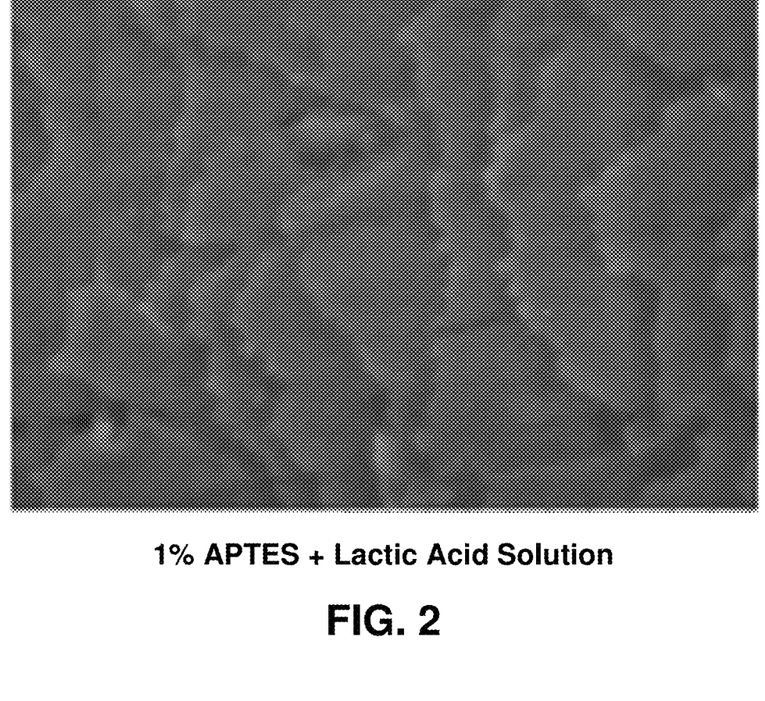
FIG. 2 is a SEM image which shows the surface of hair treated by a composition containing 1% by weight APTES and 0.6% by weight lactic acid in water. There are no solid depositions on the hair surface. The image demonstrates that the combination of lactic acid and APTES reduced or inhibited the polymerization and/or deposition of APTES on the hair surface, and thus, improved the penetration of APTES into the hair fiber.
Figure 3:
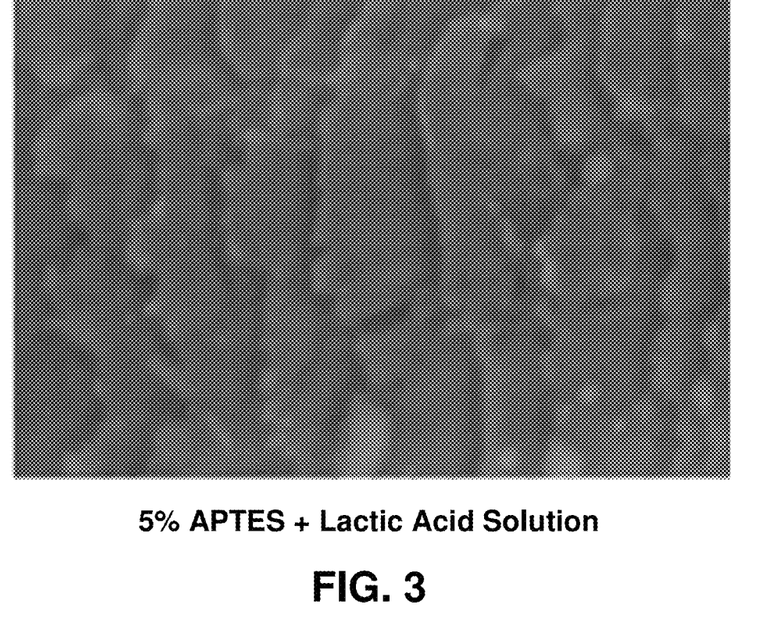
FIG. 3 is a SEM image which shows the surface of hair treated by a composition containing 5% by weight APTES and 3% by weight lactic acid in water. There are no solid depositions on the hair surface. The image demonstrates that the combination of lactic acid and APTES reduced or inhibited the polymerization of APTES on the hair surface, and thus, improved the penetration of APTES into the hair fiber.
Figure 4:
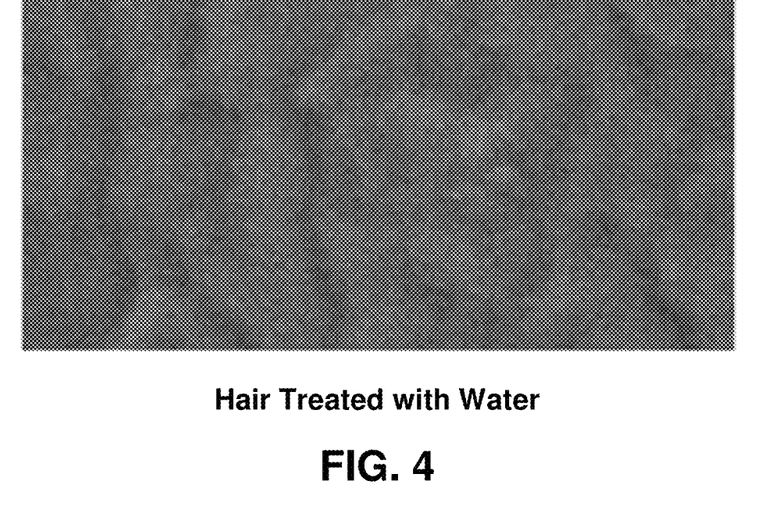
FIG. 4 is a SEM image of the surface of a hair fiber treated with water only.
Figure 5:
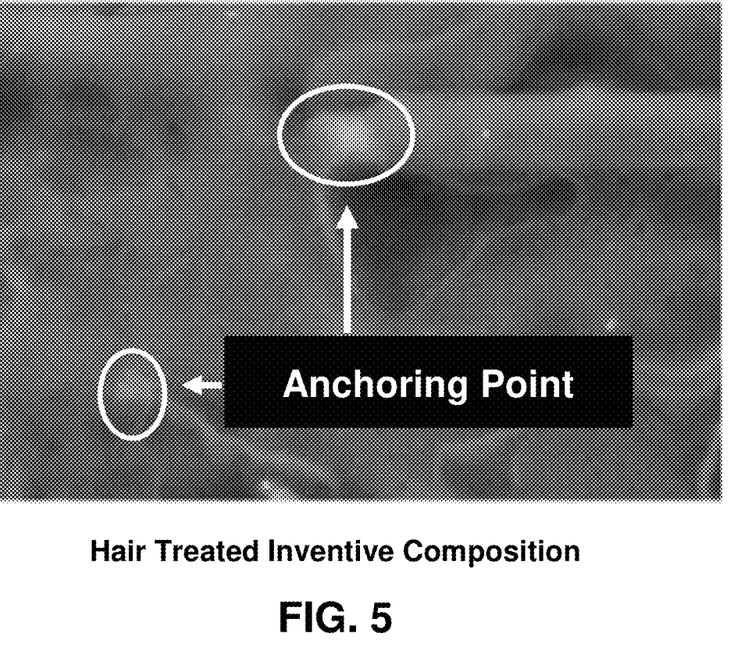
FIG. 5 is a SEM image of the surface of a hair fiber treated with the inventive composition. The image depicts the formation of a film on the hair after being treated with the inventive composition comprising the first and the second phases.

Other than in the operating examples, or where otherwise indicated, all numbers expressing quantities of ingredients and/or reaction conditions are to be understood as being modified in all instances by the term "about," meaning within 10% to 15% of the indicated number.

The term "comprising" (and its grammatical variations) as used herein is used in the inclusive sense of "having" or "including" and not in the exclusive sense of "consisting only of". The terms "a" and "the" as used herein are understood to encompass the plural as well as the singular.

"At least one" as used herein means one or more and thus includes individual components as well as mixtures/combinations.

The term "water-soluble metal salt" as used herein is understood to mean any organic or inorganic metal salt having a solubility of more than 0.2 grams at 25 degrees Celsius per liter of water.

The term "emulsifier free" as it is used herein means that while it is preferred that no emulsifiers be present in the composition, it is possible to have very small amounts of emulsifiers in the compositions of the invention provided that these amounts do not materially affect at least one, preferably most, of the advantageous properties of the compositions of the invention. In particular, "emulsifier free" means that emulsifiers can be present in the composition at an amount of less than about 0.25% by weight, typically less than about 0.1% by weight, typically less than about 0.05% by weight, and more typically 0% by weight, based on the total weight of the composition as a whole.

The compositions and methods of the present invention can comprise, consist of, or consist essentially of the essential elements and limitations of the invention described herein, as well as any additional or optional ingredients, components, or limitations described herein or any otherwise useful ingredient found in personal care compositions intended for application to hair.

The present invention also relates to methods for treating a keratinous substrate such as hair.

It was surprisingly and unexpectedly discovered that the composition of the present invention provided an aesthetically pleasing look to the hair of added volume, clean feel, shine, and styling properties, while not sacrificing the functional benefits of the composition.

It was also surprisingly and unexpectedly discovered that the composition of the present invention provided an enhanced style memory and greater style control resulting in an "invisible hold," a desirable lightly coated, touchable feel to the hair, added shine, and significantly improved cosmeticity over traditional hair treatment and styling products.

First Phase

Alkoxysilane

According to the present invention, compositions comprising at least one alkoxysilane having at least one solubilizing functional group and amino substituent are provided. In accordance with the present invention, the alkoxysilane having at least one solubilizing functional group and amino substituent.

As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents.

Suitable solubilizing functional groups for use in accordance with the present disclosure include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

The at least one alkoxysilane present in the composition comprises at least one solubilizing functional group, which may be identical or different, such as those previously defined.

The at least one alkoxysilane having at least one solubilizing functional group and amino substituent present in the composition of the present disclosure may comprise at least one silicon atom, for example, one silicon atom.

The at least one alkoxysilane having at least one solubilizing functional group and amino substituent present in the composition may, in at least one embodiment, comprise two or three alkoxy functions. In another embodiment, the alkoxy functional groups are chosen from methoxy and ethoxy functional groups.

According to one embodiment, the at least one alkoxysilane having at least one solubilizing functional group and amino substituent present in the composition of the present disclosure is chosen from compounds of formula (I):

wherein:

$R_4$ is chosen from OR' groups;

$R_5$ is chosen from OR" groups;

$R_6$ is chosen from OR'" groups;

$R_1$, $R_2$ are chosen from hydrogen;

$R_3$, R', R", R'", which may be identical or different, are chosen from linear and branched, saturated and unsaturated hydrocarbon groups, optionally bearing at least one additional chemical group, wherein R', R", and R'" may also be chosen from hydrogen.

In at least one embodiment, the R', R", and R'" groups are chosen from $C_1$-$C_{12}$ alkyl, $C_6$-$C_{14}$ aryl, $C_1$-$C_8$ alkyl-$C_6$-$C_{14}$ aryl, and $C_6$-$C_{14}$ aryl-$C_1$-$C_8$-alkyl radicals.

Particularly preferred alkoxysilanes having at least one solubilizing functional group and at least one amino substituent include alkoxysilanes comprising a silicone atom. Suitable examples include those of formula R(4-n)SiXn, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Possible examples of useful alkoxysilanes include 3-mercaptopropyltriethoxysilane and aminoalkyltrialkoxysilanes such as 3-aminopropyltriethoxysilane, as described in French Patent Application No. FR 2 789 896.

In another embodiment, the useful alkoxysilanes of the present invention may be alkoxysilanes which carry a group having a cosmetic functional group, such as aromatic nitro dyes or anthraquinone, napthoquinone, benzoquinone, azo, xanthene, triarylmethane, azine, indoaniline, indophenolic or indoamine dyes; groups having a reductive effect, such as thiol groups, sulphinic acid or sulphinic salt, it being possible for these alkoxysilanes to carry a solubilizing non-hydrolysable group such as amino groups, carboxylic acids, sulphonic acids, sulphates, quaternary ammoniums, polyalcohols, polyether and phosphates. One possible example includes aminopropyl-N-(4,2-dinitrophenyl)aminopropyldiethoxysilane. Compounds of this kind are described, for example, in Patent Application EP 1 216 023.

The alkoxysilanes of the present disclosure may be amino aryl alkoxysilanes. Possible examples include but are not limited to the following compounds:

3-(m-aminophenoxy)propyltrimethoxysilane, of the formula:

provided by GELEST, p-aminophenyltrimethoxysilane, of formula:

provided by GELEST, and
N-(2-aminoethylaminomethyl)phenethyltrimethoxysilane, of the formula:

provided by GELEST.

In another embodiment the at least one alkoxysilane having at least one solubilizing functional group and at least one amino substituent is a trialkoxysilane.

In a preferred embodiment, the at least one alkoxysilane having at least one solubilizing functional group and at least one amino substituent present in the composition of the present disclosure is a γ-aminopropyltriethoxysilane, also known as 3-aminopropyltriethoxysilane.

The at least one alkoxysilane having at least one solubilizing functional group and at least one amino substituent of the present invention is soluble in both oil and water.

The at least one alkoxysilane having at least one solubilizing functional group and at least one amino substituent is employed in an amount ranging from about 0.01 to about 30% by weight, such as from about 0.1 to about 25% by weight, and from about 0.5 to about 20% by weight, based on the total weight of the first phase of the composition of the present invention.

Water-Soluble Metal Salt

The at least one water-soluble metal salt of the present invention may be selected from a large number of compounds, wherein the metal donor may be selected from Ti, V, Cr, Mn, Fe, Co, Ni, Cu, Zn, Se, Sr, Be, Ba, Ca, Mg, Al and Mo.

The at least one water-soluble metal salt of the present invention may be chosen from polyvalent metal salts, including divalent metal salts.

The at least one water-soluble metal salt of the present invention may be also chosen from chloride, bromide, fluoride, iodide, sulfate, nitrate, phosphate, citrate, acetate salts, carboxylic acid salts and mixtures thereof.

The at least one water-soluble metal salt of the present invention is preferably a divalent metal salt.

Examples of the at least one water-soluble metal salt are zinc chloride, magnesium chloride, ferrous chloride, manganese chloride, cupric chloride, calcium chloride, cobalt dichloride, zinc sulfate, magnesium sulfate, ferrous sulfate, manganese sulfate, copper sulfate, cobalt sulfate, zinc acetate, magnesium acetate, ferrous acetate, manganese acetate, cupric acetate, calcium acetate, cobalt acetate, magnesium citrate, ferrous citrate, manganese citrate, calcium chloride, calcium citrate and mixtures thereof.

The at least one water-soluble metal salt of the present invention is preferably a divalent metal chloride salt such as magnesium sulfate.

The at least one water-soluble metal salt of the present invention is present in an amount ranging from 0.01% to about 20% by weight, preferably from about 0.05% to about 10% by weight, more preferably from about 0.1% to about 5% by weight, based on the total weight of the first phase of the composition of the present invention.

Acidifying Agent

The compositions of the present invention comprise at least one acidifying agent. The pH of said compositions may be adjusted to the desired value via at least one acidifying agent.

Among the at least one acidifying agent, non-limiting mention may be made, by way of example, of mineral or organic acids such as hydrochloric acid, orthophosphoric acid, sulfuric acid, sulfonic acids, and carboxylic acids, for instance acetic acid, tartaric acid, citric acid, and lactic acid.

The at least one acidifying agent of the present invention is preferably lactic acid.

The at least one acidifying agent of the present invention is present in an amount ranging from 0.01% to about 40% by weight, preferably from about 0.05% to about 30% by weight, more preferably from about 0.1% to about 20% by weight, based on the total weight of the first phase of the composition of the present invention.

Cosmetically Acceptable Carrier

The composition of the invention also contains at least one cosmetically acceptable carrier comprising water.

The cosmetically acceptable carrier comprising water may include an organic solvent. Thus the cosmetically acceptable carrier may be composed solely of water, or it may be composed of a mixture of water and at least one organic solvent, chosen from C1-C4 lower alcohols, polyols, and polyol monoethers.

The cosmetically acceptable carrier comprising water is typically present in an amount of from about 1% to about 99%, from about 2% to about 90%, or from about 5.0% to about 80% by weight, based on the total weight of the first phase of the composition of the present invention.

Second Phase

Silsesquioxane Resin

The compositions of the present invention comprise at least one silsesquioxane resin.

Examples of silsesquioxane resins of the present invention are alkyl silsesquioxane resins which are silsesquioxane homopolymers and/or copolymers having an average siloxane unit of the general formula $R^1_n SiO_{(4-n)/2}$, wherein each $R_1$ is independently chosen from a hydrogen atom and a $C_1$-$C_{10}$ alkyl group, wherein more than 80 mole % of $R_1$ represent a $C_3$-$C_{10}$ alkyl group, n is a value of from 1.0 to 1.4, and more than 60 mole % of the copolymer comprises $R_1SiO_{3/2}$ units.

Preferably, the silsesquioxane resin used is one where $R_1$ is a $C_1$-$C_{10}$, preferably a $C_1$-$C_4$ alkyl group, and more preferably a propyl group. A preferred silsesquioxane resin of the present invention is polypropylsilsesquioxane resin or t-propyl silsesquioxane resin ("t-propyl resin"). The t-propyl resin is commercially available in a blend from Dow-Corning under the tradename Dow Corning® 670 Fluid.

The at least one silsesquioxane resin may be present in an amount ranging from about 0.01% to about 35% by weight, such as from about 0.1% to about 25% by weight and such as from about 1% to about 15% by weight, based on the total weight of the second phase of the composition of the present invention.

Volatile Solvent

The second phase of the invention also contains at least one volatile solvent.

The expression "volatile solvent" means any non-aqueous medium capable of evaporating on contact with keratinous substrates such as hair and skin in less than one hour at room temperature and atmospheric pressure.

Examples of suitable volatile solvents include volatile hydrocarbon-based oils such as, for example, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isododecane, isodecane, isohexadecane, and for example, the oils sold under the trade names of Isopar or Permethyl, the $C_8$ to $C_{16}$ branched esters such as isohexyl or isodecyl neopentanoate, alcohols, and their mixtures. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
|---|---|
| Isododecane | 43 |
| Isohexadecane | 102 |
| Isodecyl neopentanoate | 118 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatile solvent may also be chosen from volatile silicone oils, which may be linear or cyclic, having a viscosity, at room temperature, of less than or equal to 6 cSt, and having from 2 to 7 silicon atoms, optionally substituted with alkyl or alkoxy groups of 1 to 10 carbon atoms.

Examples of suitable volatile silicone oils include, but are not limited to, those listed in Table 2 below.

TABLE 2

| Compound | Flash Point (° C.) | Viscosity (cSt) |
|---|---|---|
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

TABLE 2-continued

| Compound | Flash Point (° C.) | Viscosity (cSt) |
|---|---|---|
| PDMS DC 200 (5 cSt) from Dow Corning | 134 | 5 |
| PDMS DC 200 (3 St) from Dow Corning | 102 | 3 |

The preferred volatile solvent in the present invention is isododecane, commercially available from INEOS.

The at least one volatile solvent is generally employed in an amount ranging from about 0.01% to about 99% by weight; such as from about 0.1% to about 75% by weight; such as from about 1% to about 60% by weight, based on the total weight of the second phase of the composition of the present invention.

The first and/or second phase of the compositions of the present disclosure may also contain non-volatile solvents.

Examples of suitable non-volatile solvents include, but are not limited to, polar oils and non-polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, and also including, for example, octyldodecyl neopentanoate, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

The at least one non-volatile solvent may be employed in an amount ranging from about 0.01% to about 99% by weight; such as from about 0.1% to about 75% by weight; such as from about 1% to about 60% by weight, based on the total weight of the first phase of the second phase of the composition of the present invention.

The compositions of the present invention will comprise the first and second phases in various proportions to one another. Thus, the proportion by % weight (or weight ratio) of the first phase to second phase may be as follows: 10:90, 20:80, 50:50, 80:20, 90:10.

The cosmetically acceptable carrier comprising water of the first phase can also be present in the compositions of the present invention in the amount of about 90%, 80%, 70%, 60%, 50%, 40%, 30%, 20%, 10%, based on the total weight of the composition. The cosmetically acceptable carrier comprising water of the first phase can also be present in the compositions of the present invention in the amount of about 10%, 20%, 30%, 40%, 50%, 60%, 70%, 80%, 90%, based on the total weight of the composition. Additionally the amount of the cosmetically acceptable carrier in the composition of the present invention can be any combination of the above values, for example from about 20% to about 90% by weight, or from about 50% to about 60% by weight based on the total weight of the compositions. The cosmetically acceptable carrier comprising water of the first phase can also contain any one or a combination of the volatile solvents described above.

Auxiliary Ingredient

The first and second phases of the composition(s) of the present invention may also comprise auxiliary ingredients, for instance those chosen from the non-exhaustive list such as emulsifiers, rheology-modifying agents, film-forming agents, antioxidants, surfactants, sunscreens, sequestering agents, softeners, antifoams, basifying agents, gelling agents, wetting agents, thickening agents, spreading agents, dispersants, plasticizers, preservatives, pigments, proteins, ceramides, vitamins, mineral fillers, clays, colloidal minerals, nacres, nacreous agents, fragrances, peptizers, preserving agents, reducing agents, oxidizing agents, permanent or temporary dyes, pH adjusters, fixing or non-fixing polymers, silicones, mineral, organic or plant oils, plant extracts, volatile solvents, non-volatile solvents, oxyethylenated or non-oxyethylenated waxes, paraffins, fatty acids, and the like.

The person skilled in the art will ensure that any auxiliary ingredient and their amount are selected in such a way as to cause no detriment to the properties of the first phase, second phase and compositions disclosed herein.

The at least one auxiliary ingredient may be present in an amount ranging from 0.001% to 50% by weight, relative to the total weight of the entire composition.

The compositions disclosed herein may take the form of a spray, such as a spray gel, a gel, or lotion. The compositions may also be provided as rinse-off or leave-in products.

The compositions of the present invention may be packaged, for example, in a pump dispenser bottle customary in cosmetology.

Another embodiment disclosed herein is a cosmetic treatment method for the hair, for example a hair styling method, comprising applying an effective amount of the composition disclosed herein to wet or dry hair, and rinsing the composition off or leaving it in after an optional exposure time or an optional drying step.

In one preferred embodiment, the composition is used as a leave-in product.

Further disclosed herein is the use of the cosmetic compositions of the present invention for shaping hair and/or retaining a hairstyle.

Not to be bound by any particular theory, the at least one acidifying agent of the present invention functions to control the pH and prevent the at least one alkoxysilane having at least one solubilizing functional group and at least one amino substituent from polymerizing in order to allow it in its monomeric form to penetrate and anchor into the hair fiber.

Not to be bound by any particular theory, the at least one silsesquioxane resin of the present invention associates with the at least one alkoxysilane having at least one solubilizing functional group and at least one amino substituent of the present invention to form a film on the hair fiber.

One embodiment of the present invention includes a bi-phasic composition having a first phase including alkoxysilane having at least one solubilizing functional group and at least one amino substituent, a water-soluble metal salt, an acidifying agent, and water, and a second phase including a silsesquioxane resin and a volatile solvent. Preferably, the bi-phasic composition is sprayable, that is, it is in spray form.

A preferred embodiment of the present invention includes a sprayable biphasic hair styling composition comprising the above-described composition.

The term "bi-phasic appearance" as used herein is defined as having two visually observed layers.

When the composition of the present invention is a bi-phasic hair styling composition, the composition is shaken to temporarily mix the two layers and then applied onto damp or dry hair. The hair is then allowed to air dry or heat styled.

In one embodiment, the composition of the present invention is emulsifier-free.

In another embodiment, the composition of the present invention comprises at least one emulsifier to yield a single phase composition.

The examples which follow are given by way of illustration and not of limitation of the present invention.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Not withstanding that the numerical ranges and parameters setting forth the broad scope of the invention are approximations, unless otherwise indicated the numerical values set forth in the specific examples are reported as precisely as possible.

EXAMPLES

Example 1: Aqueous and Anhydrous Phases of the Invention

| First Phase | |
| --- | --- |
| INCI Name | (#P477053 G) % by weight |
| Magnesium Sulfate | 1.0 |
| Lactic Acid | 3.0 |
| AMINOPROPYL TRIETHOXYSILANE (APTES) | 2.0 |

-continued

First Phase

| INCI Name | (#P477053 G) % by weight |
|---|---|
| Ethylhexylglycerin | 0.09 |
| Phenoxyethanol | 0.8 |
| Water | QS to 100 |

Process of Making First Phase

Water was added into the main beaker and mixed at medium speed. Magnesium sulfate, lactic acid, aminopropyl triethoxysilane, ethylhexylglycerin, and phenoxyethanol were added one at a time into the main beaker and mixed well between each addition. The resulting mixture was agitated until the all raw materials were completely dissolved.

Second Phase

| INCI Name | (#P477056 C) % by weight |
|---|---|
| HYDROGENATED STYRENE/METHYL STYRENE/INDENE COPOLYMER (Regalite R1100) | 4.0 |
| C12-15 Alkyl Benzoates | 5.0 |
| Isopropyl Myristate | 13.0 |
| POLYPROPYLSILSESQUIOXANE | 6.31 |
| Isododecane | 54.16 |
| Isohexadecane | 17.23 |
| Fragrance | 0.3 |

Process of Making Second Phase

Isododecane was added into the main beaker. Hydrogenated Styrene/Methyl Styrene/Indene Copolymer was slowly dispersed into the main beaker and the mixture was heated to 45° C. The mixture was agitated until the raw materials were completely dissolved. The remainder of the raw materials were added to the main beaker, one at a time, and agitated until the mixture became clear.

Example 2: First and Second Phases at Various Ratios (Wt %/wt %) for Use in the Compositions of the Invention

| first phase | 10 | 20 | 30 | 40 | 50 | 60 | 70 | 80 | 90 |
|---|---|---|---|---|---|---|---|---|---|
| second phase | 90 | 80 | 70 | 60 | 50 | 40 | 30 | 20 | 10 |

The compositions comprising the first and second phases in various proportions to each other as tabulated above were biphasic in appearance. As the proportion of the first phase to the second phase changes in the composition of the present invention, varying cosmetic effects and styling performance on the hair were observed. With 10% by weight of the second phase in the total weight of the composition, a light weight, smooth, and natural finish was observed on the hair. This low percentage of the anhydrous phase was found to be ideal for consumers with fine hair types. With 90% by weight of the second phase in the total weight of the composition, a more rigid, high shine finish with added texture was observed on the hair. This was found to be ideal for consumers with coarse hair types. Thus, the proportions of the first phase to the second phase may be varied within the weight ratio spectrum to create different products for all individual hair types.

Example 3: Salon Testing on the Hair of 12 Heads of Human Panelists

The spray bottle was aggressively shaken to thoroughly mix the two phases in the container. The contents were then sprayed onto damp hair and the hair was either allowed to air dry or it was blow dried. Once the hair was dry, a curling iron or flat iron was used to further style the hair.

| Spray | Cosmetic Attributes Observed from the Salon Test |
|---|---|
| First phase alone | Product gives a clean and light feel to the hair. It provides good detangling property, softness, smoothness, extremely, shine, conditioned ends, soft to medium hold, control of static electricity and better control of frizz. |
| Second phase alone | The product is a little heavy with a greasy feel. It weights hair down. It is suitable only for coarse hair type. |
| Combination of first and second phases in a bi-phase Spray composition | The Bi-phase composition is unique for its volume, body, shine, fast drying, and not greasy. The product feels natural/almost nothing, and clean without build up. It has a light weight with a silky feel. |

The foregoing description illustrates and describes the present disclosure. Additionally, the disclosure shows and describes only the preferred embodiments of the disclosure, but, as mentioned above, it is to be understood that it is capable of changes or modifications within the scope of the concept as expressed herein, commensurate with the above teachings and/or skill or knowledge of the relevant art. The embodiments described hereinabove are further intended to explain best modes known of practicing the invention and to enable others skilled in the art to utilize the disclosure in such, or other, embodiments and with the various modification required by the particular applications or uses disclosed herein. Accordingly, the description is not intended to limit the invention to the form disclosed herein. Also, it is intended that the appended claims be construed to include alternative embodiments.

What is claimed is:

1. A composition for styling hair comprising:
(a) a first phase comprising:
  i. about 0.01 to about 30% by weight, based on the total weight of the first phase, of 3-aminopropyltriethoxysilane;
  ii. about 0.01 to about 20% by weight, based on the total weight of the first phase, of at least one water-soluble metal salt chosen from magnesium sulfate, sodium sulfate, calcium sulfate, and a mixture thereof;
  iii. about 0.01 to about 40% by weight, based on the weight of the first phase, of at least one acidifying agent chosen from lactic acid, citric acid, acetic acid, and a mixture thereof; and
  iv. at least one cosmetically acceptable carrier comprising water;
(b) a second phase comprising:
  i. about 0.01 to about 35% by weight, based on the total weight of the second phase, of a polypropylsilsesquioxane resin; and
  ii. at least one volatile solvent.

2. The composition of claim 1, wherein (a)(i) is present in an amount of from about 0.5 to about 20% by weight, (a)(ii) is present in an amount of from about 0.1 to about 5% by weight, and (a)(iii) is present in an amount of from about 0.1 to about 20% by weight, based on the weight of the first phase; and (b)(i) is present in an amount of from about 1 to about 15% by weight, based on the total weight of the second phase.

3. The composition of claim 1, wherein (a)(iv) further comprises volatile or non-volatile solvents.

4. The composition of claim 1, wherein (a)(iv) is present in an amount of from about 1 to about 99% by weight, based on the weight of the first phase.

5. The composition of claim 1, wherein (b)(ii) is chosen from isododecane, isohexadecane, and mixtures thereof.

6. The composition of claim 1, wherein (b)(ii) is present in an amount of from about 0.01 to about 99% by weight, based on the total weight of the second phase.

7. The composition of claim 1, wherein (b) further comprises at least one non-volatile solvent.

8. The composition of claim 1, wherein the weight ratio of (a) to (b) is from 10:90 to 90:10.

9. The composition of claim 1, wherein the weight ratio of (a) to (b) is 20:80 to 80:20.

10. The composition of claim 1, wherein the composition has a bi-phasic appearance.

11. The composition of claim 1, wherein the composition is in a spray form.

12. The composition of claim 1, wherein the composition is emulsifier free.

13. A composition for styling hair comprising:
 (c) from about 0.2 to about 2% by weight of 3-aminopropyltriethoxysilane;
 (d) from about 0.5 to about 5.5% by weight of polypropylsilsesquioxane resin;
 (e) from about 0.1% to about 1% by weight of magnesium sulfate;
 (f) from about 0.1 to about 3% by weight of lactic acid;
 (g) from about 9% to about 85% by weight of water; and
 (h) from about 5% to about 70% by weight of volatile solvent;
 all weights being based on the total weight of the composition.

14. A method of styling hair comprising contacting the hair with the composition comprising:
 (a) a first phase comprising:
  i. about 0.01 to about 30% by weight, based on the total weight of the first phase, of 3-aminopropyltriethoxysilane;
  ii. about 0.01 to about 20% by weight, based on the total weight of the first phase, of at least one water-soluble metal salt chosen from magnesium sulfate, sodium sulfate, calcium sulfate, and a mixture thereof;
  iii. about 0.01 to about 40% by weight, based on the weight of the first phase, of at least one acidifying agent chosen from lactic acid, citric acid, acetic acid, and a mixture thereof; and
  iv. at least one cosmetically acceptable carrier comprising water;
 (b) a second phase comprising:
  i. about 0.01 to about 35% by weight, based on the total weight of the second phase, of a polypropylsilsesquioxane resin; and
  ii. at least one volatile solvent.

15. The method of claim 14, wherein (a)(iv) further comprises volatile or non-volatile solvents.

16. The method of claim 14, wherein (b) further comprises at least one non-volatile solvent.

17. The method of claim 14, wherein (b)(ii) is chosen from isododecane, isohexadecane, and mixtures thereof.

18. The composition of claim 13 that is emulsifier free.

19. The method of claim 14, wherein the composition is emulsifier free.

* * * * *